Feb. 12, 1974 H. A. JOHNSON, JR Plant Pat. 3,473
STRAWBERRY PLANT
Filed June 7, 1972
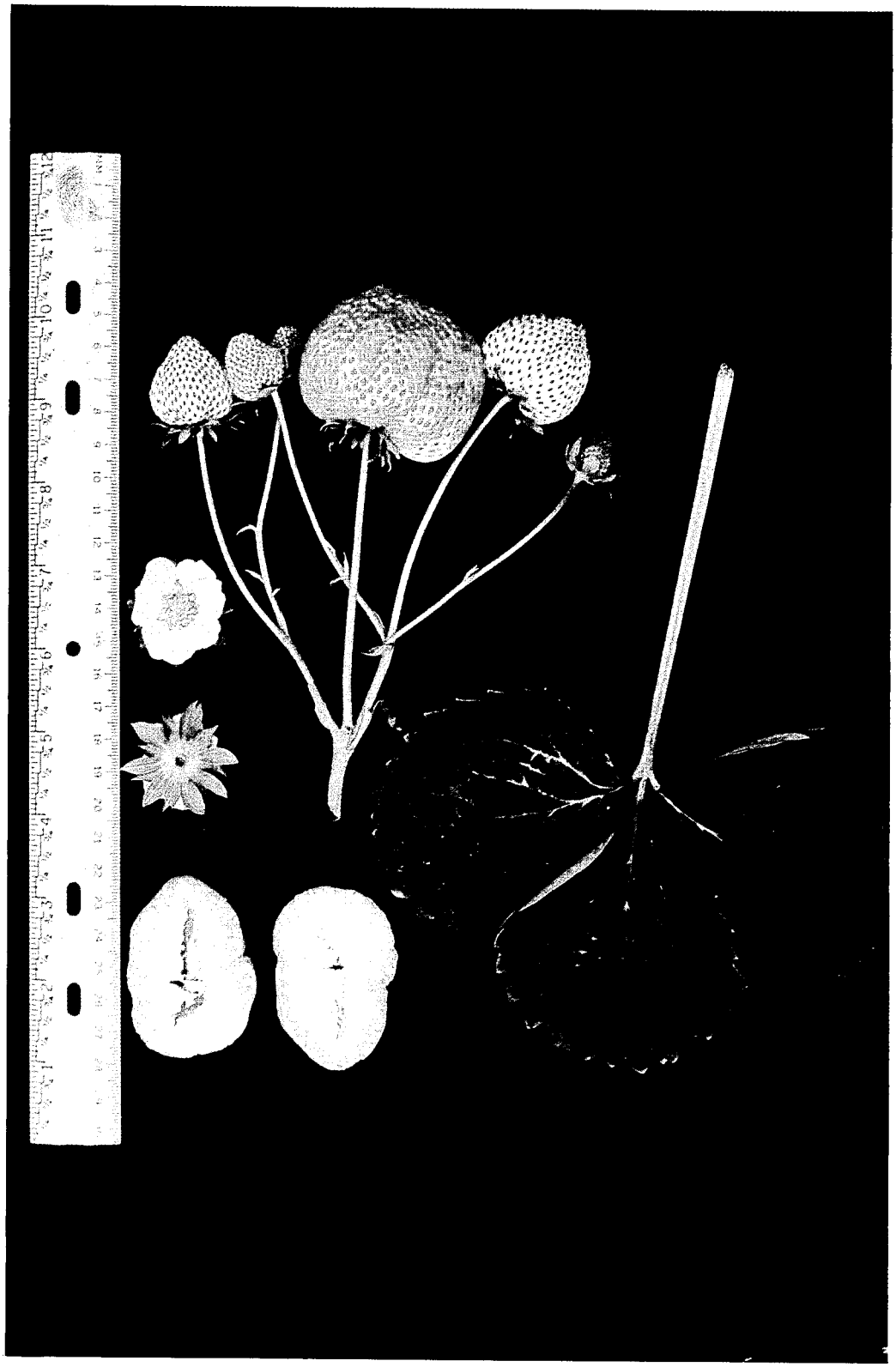

United States Patent Office

Plant Pat. 3,473
Patented Feb. 12, 1974

3,473
STRAWBERRY PLANT

Harold A Johnson, Jr., Watsonville, Calif., assignor to Driscoll Strawberry Associates, Inc., Watsonville, Calif.

Filed June 7, 1972, Ser. No. 260,693
Int. Cl. A01h 5/03
U.S. Cl. Plt.—49 1 Claim This invention relates to a new and distinct variety of strawberry plant which is the result of a cross of the unpatented variety known as The Driscoll Strawberry Associates Selection B5 and The Driscoll Strawberry Associates Selection United States Letter Patent 2,612.

The seedling resulting from the aforementioned cross were grown and asexually multiplied in Shasta County, Calif., and tested in the fruiting beds on the property of member growers of Driscoll Strawberry Associates, Inc. Clones of the seedlings were also held at the Propagation Nursery in Shasta County. One plant was selected from the aforementioned group of seedlings and further asexually reproduced in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Plant parts of the new variety, typical in size, shape and color are pictured in the accompanying photograph. A berry in cross section illustrates flesh color and characteristic core cavity. The inflorescence pictured illustrates typical branching and relative size during May. The pedicel holding the primary berry originates from a secondary peduncle in the majority of inflorescences rather than from the axial as is shown in this picture. The number of secondary peduncles is two in this picture and it is a typical number. The common peduncle in this picture has been broken off at a point before it joins the plant crown, but the length of the common peduncle is considered short as is the total length of the inflorescence. The leaf pictured does not show the basal bract of the petiole. The leaflets shown are recently matured leaflets and have not started to show the marginal burning that is typical in this variety when the leaflets are mature. The cupping upward of the margins of the leaflet is typical.

This novel new summer planted spring variety has a medium to large plant with characteristic dark leaflets. The marginal burns of the serrations appear to be a normal plant characteristic which is not necessarily detrimental to the plant growth or production. This variety has the ability to produce consistently large fruit size early in the spring after summer planting. The new variety continues in this production through the season and even though it cycles somewhat, it does not reach a period during the year where there is no cropping. Excellent fruit size is maintained throughout the summer period if the plant vigor is maintained. Early in the spring, fruit color is not as uniform as later in the season. The fruit size and ease in picking makes this new variety quite acceptable as a shipping strawberry to interstate markets. Shipping and holding tests to this point in time have proven satisfactory. This new variety produces a plant that is darker in leaf color most of the early season than the Driscoll Strawberry Associates variety. Nedspride, Plant Patent 2,796. It is considered a medium to large plant, but the petiole length is not as long as that of the Nedspride. Its leaflets are equal to, to slightly larger in diameter than the Nedspride and tend to cup upward at the margins to a greater degree than Nedspride. The petiolule of the new variety is consistently shorter than Nedspride and is comparatively short. Both the common peduncle and the total length of its inflorescence is shorter than that of the Nedspride and its flowers are conspicuously noticeable above the plant only during the spring period. The number of secondary peduncles produced by this variety is normally less than that of the Nedspride and the diameter of individual pedicels is equal to or smaller than Nedspride. Primary and secondary berries may often ripen at the same time on a given inflorescence but normally the primary ripens first. This new variety rpoduces an abundance of pollen early in the season, an amount superior to that of Nedspride. During the spring primary berries become ribbed but not to the extent of Nedspide. As the season progresses, primary berries may remain even more globose or oblate than Nedspride. The shoulders of the fruit near the calyx remain round and not necked. The calyx is consistently smaller than that of the Nedspride variety. One of the attributes of this new variety is its ability to consistently produce good fruit size the second fruiting year. The fruit size, especially tertiaries, is conspicuously larger than that of the Nedspride variety the second fruiting year. The fruit firmness, including epidermis and flesh, however, is not as consistently firm as that of the Nedspride. The dessert quality is superior to that of Nedspride. The fruit may have inserted seed rather than exerted in contrast to the Nedspride. This new variety is quite susceptible to the disease known in California as vascular collapse especially, if it is winter planted. It normally does, however, remain a strong, vigorous plant after the spring and summer production, and during the second fruiting year, and does not appear to be susceptible to foliar dieases that contribute to summer and fall die-out which is in contrast to the Nedspride. The strawberry aroma of the fruit of this new variety is more noticeable than that of the Nedspride variety. Under normal conditions at the nursery it produces larger runner transplant crowns, but fewer per each mother plant than Nedspride. This new variety appears to be less tolerant to the two-spotted mite than the Nedspride and is also more susceptible to mildew. It has not been completely tested against the Verticillium or Red Stele diseases. As a seedling and selection, this variety withstood the natural invasions of certain virus components found in central California without losing its ability to produce.

The varietal characteristics of the novel plant, described below in detail, were observed mainly during the first fruiting season, but reference is also made to the appearance during the second fruiting year. Observations were made in the Watsonville area of California which is a cool coastal area near the Pacific Ocean. The color terminology is in accordance with Ridgeways Color Standards and Nomenclature (1912 Edition).

Plants.—Medium to large, vigorous if given ample nutrients and is kept free of the two-spotted mite. It has an extensive root system.

Leaves.—Leaflets are medium to large in size, central leaflet is mostly 7 to 9 cm. in length and width. Petioles are medium in length, mostly 15 to 20 cm. from the base of the petiolule. Petiolules are considered short, 5 to 9 mm. The leaflet serrations are medium deep and acute at the apex, often becoming necrotic as the leaflet becomes mature. Bracts are not normally present on the petiole. There is a gradual cupping upward of the leaf from the main vein to the serrations. Leaflet surface is mildly rugose. The color of the upper side of the leaflet is Dark Yellowish Green, Plate XVIII.

Runner.—Runners are vigorous, but only medium in abundance at the nursery and the fruiting bed.

Inflorescence.—The inflorescence is medium in length, mostly 15 to 20 cm. during early summer period. The common peduncle is short to medium in length, mostly 4 to 9 cm. Secondary peduncles mostly 2 in number. Primary and secondary berries may be ripening at the same time, but primary ripens first. The pedicel holding the primary berry usually originates from a peduncle but may originate at the axil of the peduncles (see illustration). Flowers are large and showy with an abundance of pollen present on anthers. Flowers are visible above the plant mainly during spring period and not as visible in later crops.

Fruit.—The first crop of berries produced during the spring after a summer planting are generally large. Subsequent crops are smaller in amount but a large size is still maintained even on secondary and tertiary berries. Primaries during May and June are mostly 40 to 45 mm. in length and 50 to 55 mm. in width. Fruit shape is mainly short-wedge to medium-conic but become globose to globose-conic even when the fruit size is large (U.S. D. A. Bulletin 1043). Shoulders are rounded at the calyx end and not necked. Fruit may color unevenly, especially during spring, with the shoulders the last to change color. Primary berries may have small longitudinal ribs but secondary and tertiary berries are usually smooth, not malshaped but the shape may vary. Seed generally remains yellow but will darken to a limited degree when exposed to direct sunlight. Seeds are generally held equal to the fruit surface but may become slightly inserted. The berry has a sweet, high dessert quality. Fruit flesh and epidermis are considered medium to good in firmness. The color of the fruit surface is Scarlet Red, Plate 1. The flesh color is Scarlet, Plate I near the epidermis, becoming near white at the core. Core size is medium to large.

Calyx.—Small to medium in diameter in comparison to fruit size, mostly 35 to 40 mm. in diameter. Sepals mainly 13 to 15 in number. Serrations are not abundant and are usually elliptic to lanceolate and acute. Sepal color on side facing the fruit is comparatively light, Light Cress Green, Plate XXXI.

I claim:

1. The new and distinct variety of strawberry plant herein described and illustrated, and identified by the characteristics enumerated above.

No references cited.

ROBERT E. BAGWILL, Primary Examiner